United States Patent
Schoon et al.

[11] Patent Number: 6,001,127
[45] Date of Patent: Dec. 14, 1999

[54] ANNULOPLASTY RING HOLDER

[75] Inventors: Thomas G. Schoon, Cedar; Deborah A. Loch, St. Paul; Kimberly A. Anderson, Eagan, all of Minn.

[73] Assignee: St. Jude Medical, Inc., St. Paul, Minn.

[21] Appl. No.: 09/052,437

[22] Filed: Mar. 31, 1998

[51] Int. Cl.⁶ ........................................................ A61F 2/24
[52] U.S. Cl. ............................................ 623/2; 623/3
[58] Field of Search ............................. 623/2, 3; 606/1, 606/2

[56] References Cited

U.S. PATENT DOCUMENTS

| | | | |
|---|---|---|---|
| 4,055,861 | 11/1977 | Carpentier et al. | 3/1.5 |
| 4,585,453 | 4/1986 | Martin et al. | 623/2 |
| 4,585,458 | 4/1986 | Kurland | 623/13 |
| 4,612,011 | 9/1986 | Kautzky | 623/2 |
| 4,629,459 | 12/1986 | Ionescu et al. | 623/2 |
| 4,679,556 | 7/1987 | Lubock et al. | 128/303 |
| 4,683,883 | 8/1987 | Martin | 128/303 |
| 4,865,600 | 9/1989 | Capentier et al. | 623/2 |
| 5,011,481 | 4/1991 | Myers et al. | 623/2 |
| 5,041,130 | 8/1991 | Cosgrove et al. | 623/2 |
| 5,061,277 | 10/1991 | Carpentier et al. | 623/2 |
| 5,290,300 | 3/1994 | Cosgrove et al. | 606/148 |
| 5,403,305 | 4/1995 | Sauter et al. | 606/1 |
| 5,415,667 | 5/1995 | Frater | 623/2 |
| 5,443,502 | 8/1995 | Caudillo et al. | 623/2 |
| 5,522,884 | 6/1996 | Wright | 623/2 |
| 5,578,076 | 11/1996 | Krueger et al. | 623/2 |
| 5,766,240 | 6/1998 | Johnson | 623/2 |
| 5,776,188 | 7/1998 | Shepherd et al. | 623/2 |
| 5,776,189 | 7/1998 | Khalid | 623/2 |
| 5,824,066 | 10/1998 | Gross | 623/2 |
| 5,824,069 | 10/1998 | Lemole | 623/2 |

*Primary Examiner*—David H. Willse
*Assistant Examiner*—Suzette Jackson
*Attorney, Agent, or Firm*—Westman, Champlin & Kelly, P.A.

[57] ABSTRACT

An annuloplasty ring and support assembly includes a ring support that has a peripheral wall with a peripheral shoulder surface, and a flange extending at generally right angles to the shoulder surface. The flange is removed or terminated in a selected portion of the peripheral wall so that the shoulder surface is unobstructed and provides a backing support against which a cutting force will be reacted when the annuloplasty ring is cut.

26 Claims, 9 Drawing Sheets

ANNULOPLASTY RING HOLDER

BACKGROUND OF THE INVENTION

The present invention relates to an annuloplasty ring holder assembly. The flexible annuloplasty ring is tied to and positioned against a shoulder and an overlying flange above the shoulder for shaping and positioning the annuloplasty ring. A cut zone is provided on the holder to permit a surgeon to cut away portions of the annuloplasty ring as needed.

Annuloplasty rings are useful in a variety of surgical procedures including mitral and tricuspid annular repair. The ring repairs the heart valve annulus and restores orifice area and normal function. In these procedures, a holder that is of the desired shape and size is provided, and the annuloplasty ring is attached to the holder. The holder secures and maintains the shape of the ring while suturing the ring into a location in a heart or other tissue.

U.S. Pat. No. 5,041,130 shows and describes an annuloplasty ring and holder wherein the edge of the holder is recessed to form a trough to position an annuloplasty ring on the surface. The annuloplasty ring is C-shaped, and does not form a full annulus.

The use of a full annulus annuloplasty ring permits a surgeon to select the amount of the ring that should be implanted, and cut away the portions of the ring that are not needed.

U.S. Pat. No. 5,011,481 also illustrates a holder for an annuloplasty ring where the holder has an annular support wall with a plurality of fingers that extend out from the support wall and have depending ends. The annuloplasty ring is supported between the holder wall and the depending ends of the fingers.

SUMMARY OF THE INVENTION

The present invention is directed toward a holder for use with annuloplasty rings which provides a substantially continuous support for the ring around its periphery to make suturing the ring to surrounding tissue more reliable, to evenly space sutures to prevent plications and to provide a cut zone where a surgeon can trim the annuloplasty ring to form a partial annuloplasty ring (C-shape). The holder is shaped to approximate the shape of the native heart valve annulus and support the flexible annuloplasty ring against an annular shoulder that has a top flange at right angles to the shoulder. In the cut zone, the flange is removed so a cut can be made through the ring. The shoulder surface provides a backing anvil surface for the ring during cutting.

The holder of the present invention can be used for supporting either a full, annular annuloplasty ring as well as a partial, C-shaped ring. When the annuloplasty ring is cut, the shoulder and flange surface of the present holder keeps the free or cut ends of the annuloplasty ring supported from movement. The cut ends are held so they do not move or displace when being sutured in place. Cutting the annuloplasty ring in the cut region of the present invention ensures that the cut edges do not move freely, but rather, remain supported.

A suture is used to securely attach the annuloplasty ring to the holder before implantation. Radial grooves or slots are formed on the top of the holder and the suture attaching the ring to the holder crosses the radial grooves. The ring-to-holder suture can easily be cut at several locations so the attaching suture and the holder can be easily removed from the ring at the time of the surgical procedure. The portion of the ring that is trimmed away to form a C-shape is removed from the holder before implantation.

The holder is preferably rigid and has open center regions so that the surgeon may see through the interior of the holder during implantation.

DETAILED DESCRIPTION OF THE PREFERRED EMBODIMENTS

Figure 1:
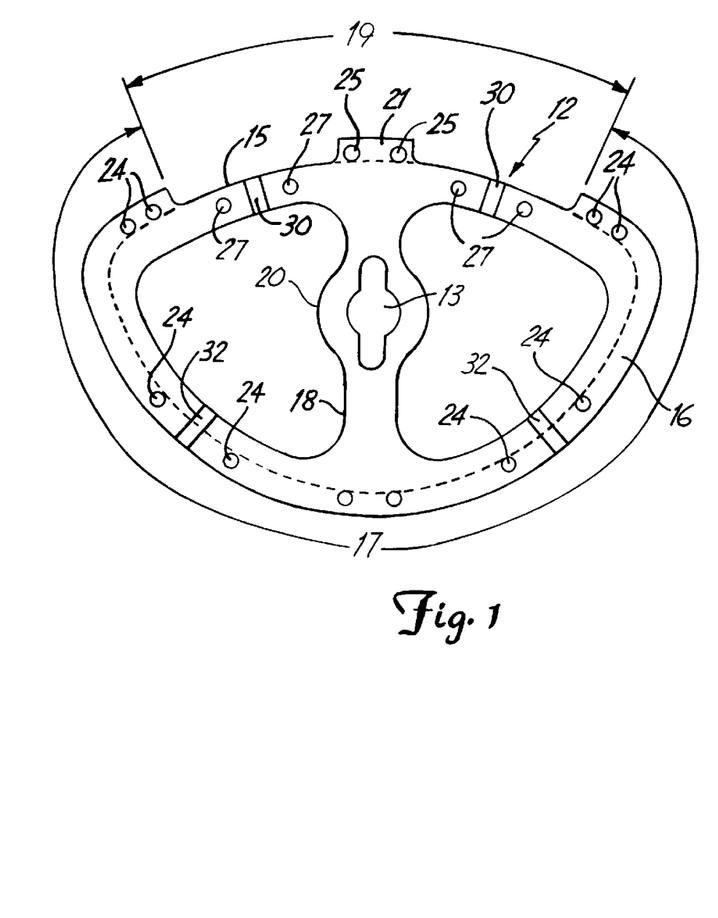
FIG. 1 is a top plan view of an annuloplasty ring holder or support made according to the first form of the present invention.
Figure 2:
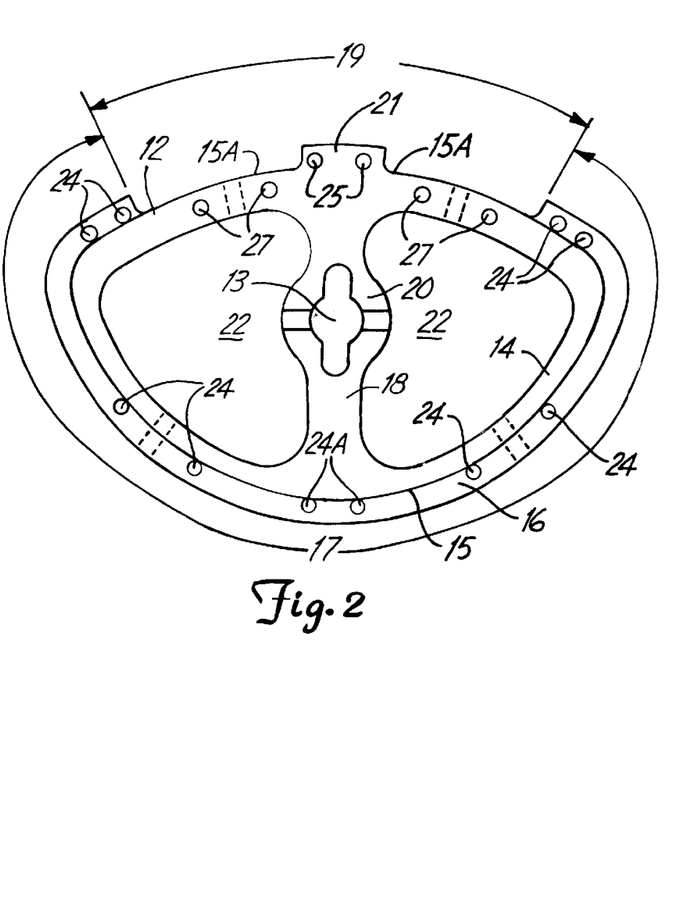
FIG. 2 is a bottom plan view of the device of FIG. 1.
Figure 3:
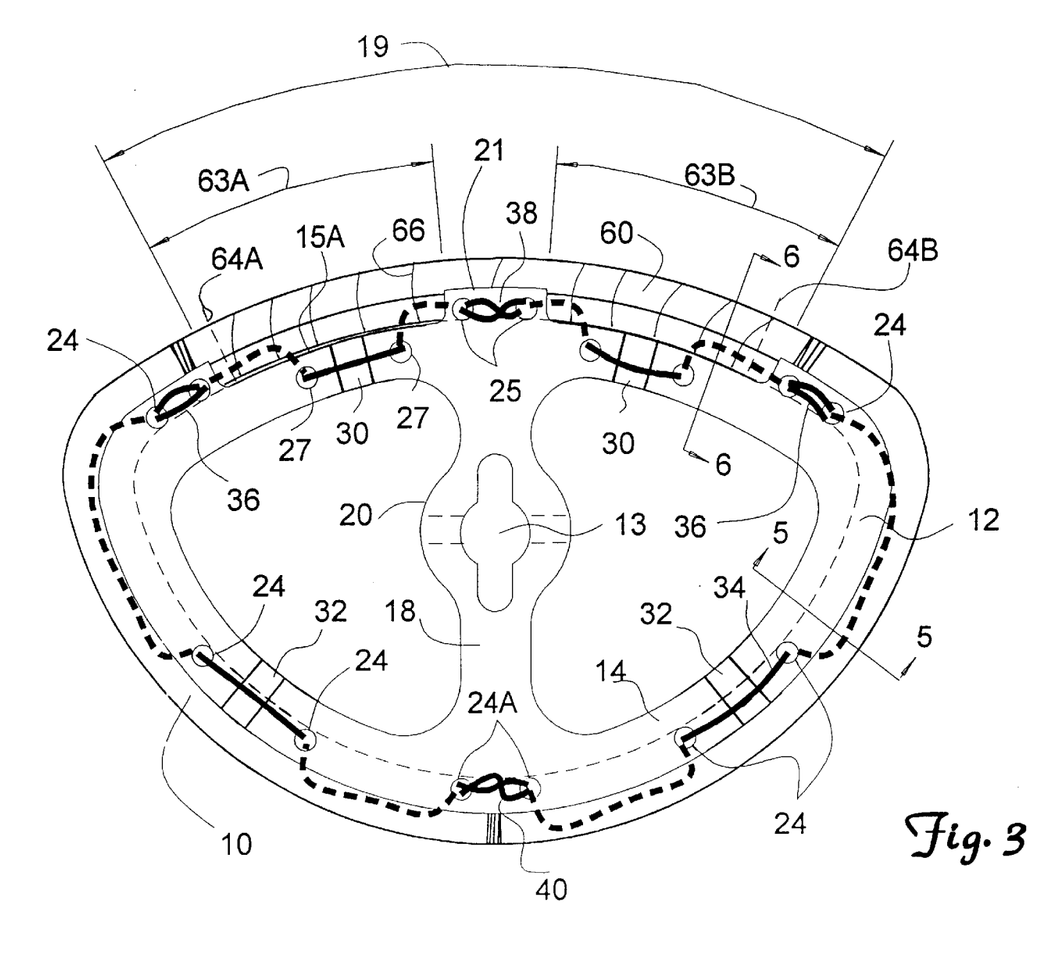
FIG. 3 is an enlarged top plan view of the ring holder of FIG. 1 showing an annuloplasty ring sutured to the ring holder.

FIGS. 1 and 2 illustrate an annuloplasty ring holder or support 12 (called a ring holder), which is for supporting a flexible annuloplasty ring 10 shown in FIG. 3. The ring holder 12 has a connector receptacle 13 for receiving a handle 96 (shown in FIG. 13) that is used for positioning the ring holder 12 and the attached annuloplasty ring 10 during the process of suturing the annuloplasty ring into place in a heart. During manufacture, the annuloplasty ring 10 and the ring holder 12 are sutured together as an assembly. If desired by the surgeon, the ring may be cut into a C-shape prior to introduction into an opening of a heart or other location.

The ring holder 12 is generally annular, and formed in a desired shape similar to that of a valve annulus of a heart valve to which the annuloplasty ring 10 is to be sutured. The ring holder can be made of any suitable biocompatible material, such as polysulfone. The holder preferably is rigid, but may be made somewhat flexible. A peripheral wall member 14 has an outer shoulder surface 15, which has an integral top flange 16 extending out from the peripheral wall 14, perpendicular to the surface 15.

The top flange 16 extends around a generally C-shaped section 17 of the ring holder 12, but the flange 16 is removed along selected portions of the wall forming a number of cutting zones indicated at 19. For example, cut zone 19 may be located near or at the trigones of the heart valve anatomy. Additional cut zones can be formed along the C-shaped section 17 to accommodate other anatomical features. The shoulder surface 15 is continuous across the cut zone. A tab 21 is provided in the center of the cut zone 19 at the same height as, or coplanar with, the flange 16. The tab 21 provides rigidity when a full annuloplasty ring is used. When forming a C-shaped ring, tab 21 retains the suture 34 on the holder as ring segment 60 is removed.

A cross arm 18 extends across the open center defined by the peripheral wall 14 of the ring holder. Alternatively, cross arm 18 may extend partially into the open center defined by the peripheral wall. Cross arm 18 has a central hub 20 in which the connector receptacle 13 is formed. The cross arm 18 leaves openings shown at 22 through which a surgeon can see the heart valve orifice when the annuloplasty ring 10 is being sutured in place. Alternatively, the holder can be an integral piece made of a transparent material which would allow viewing of the ring by the surgeon. The cross arm 18 also allows a surgeon to grab the holder with standard surgical tools, such as a hemostat.

The wall 14 is continuous, and provides a continuous support shoulder surface 15 for the annuloplasty ring 10. The top flange 16 is essentially continuous in C-shaped section 17 and provides a support opposing needle penetration forces as the ring 10 is sutured to tissue.

As shown in FIGS. 1 and 2, the ring holder 12 has a plurality of suture bores or openings 24 extending through the flange 16 at desired locations around the periphery of the C-shaped section 17. The tab 21 in the cut zone also has suture openings 25 therein. In the cut zone 19, the peripheral wall 14 is provided with through suture openings 27 on opposite sides of generally radial release or cutting grooves 30 which are recessed into the top surface of the wall 14, and across which the suture extends. The peripheral wall 14 and the flange 16 have radial grooves 32 extending between pairs of suture openings 24, as shown, so that a suture will span these grooves 32. The radial grooves 30 and 32 are deep enough to aid in severing or cutting the suture lengths that pass over the radial grooves, but end at a level high enough above the ring 10 to avoid inadvertent severing of the ring. The grooves 32 are shallower than the thickness of the flange 16.

FIG. 3 is an enlarged view showing the annuloplasty ring 10 sutured in place on the ring holder 12. The annuloplasty ring 10 can be any ring known in the art, preferably a flexible ring. The cover of the ring may have a number of stitches 66 in the cut zone 19 which are illustrated schematically, which aid in identifying the cut zone or limit fraying of the cut ends. A suture 34 is threaded through the openings, commencing at the openings 24A, then threading the suture as shown by dotted lines and solid lines proceeding clockwise, so that the suture will span the first groove 32. A first cinch knot 36 is formed near the beginning of the cut zone 19. The suture is stitched through openings 27 to span groove 30 and then is looped at the openings 25. The suture is carried clockwise around the ring and back to the openings 24A. The suture is cut and a double surgeon's knot is tied as shown at 38 at openings 25 on tab 21. Another double surgeon's knot is tied at 40 at openings 24A. Knot 40 is formed after pulling the suture ends tight, so that the span of the suture across the cutting grooves 32 is tight. The knot 38 acts as a suture anchor to hold the suture tight.

Figure 4:
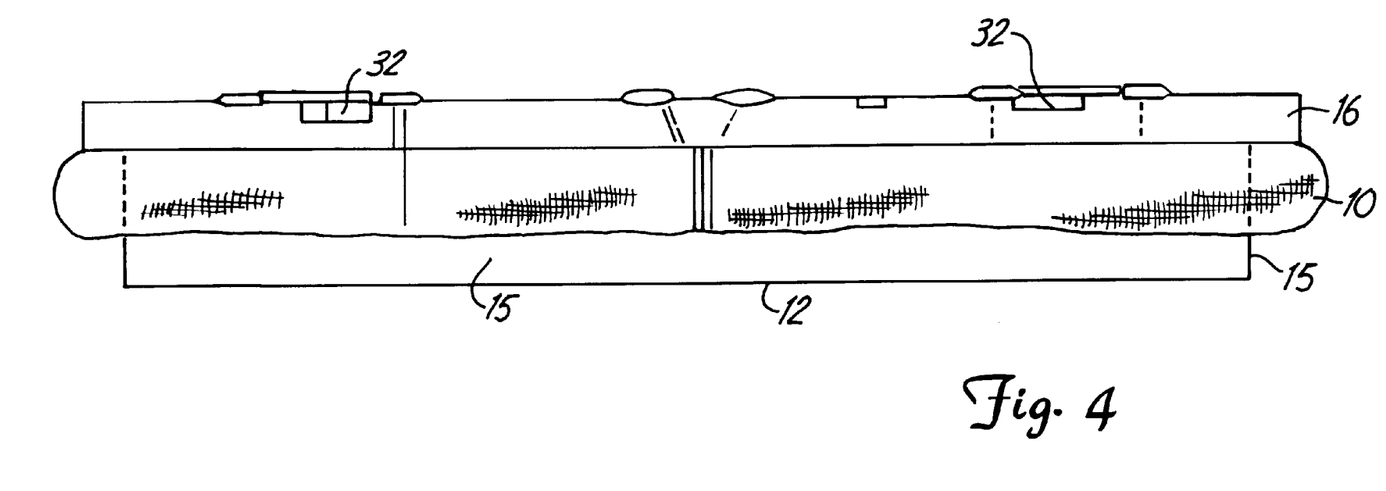
FIG. 4 is a side view of the ring holder of FIG. 3.
Figure 5:
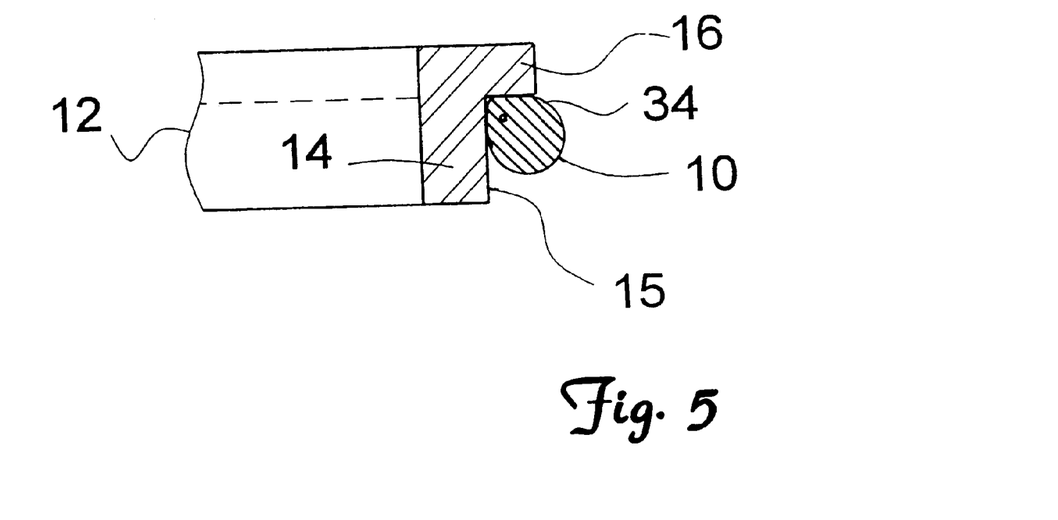
FIG. 5 is a sectional view taken as on line 5—5 in FIG. 3.
Figure 6:
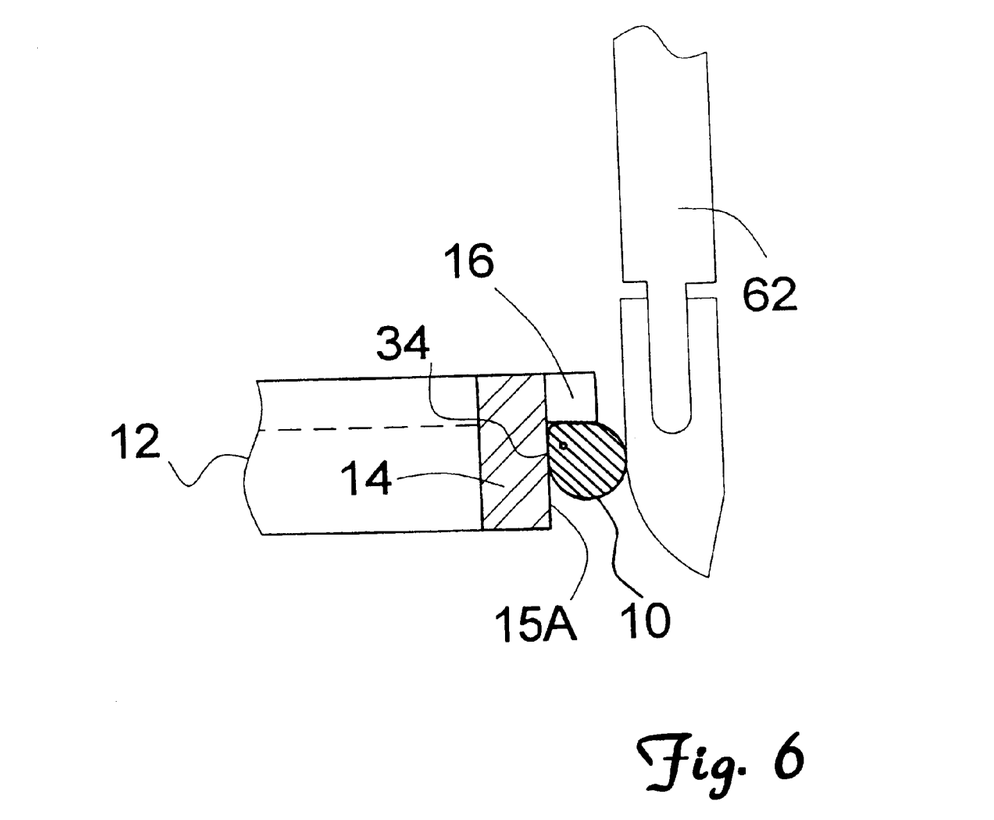
FIG. 6 is a sectional view along line 6—6 in FIG. 3.

The suture 34 is tightened and the ring 10 will be situated generally as shown in FIG. 4 with the ring 10 positioned against the flange 16 as well as the shoulder surface 15. Also see FIG. 5. A portion of the annuloplasty ring shown at 60 in FIG. 3 may be cut away if it is not needed. The present ring holder 12 provides a backing for a surgeon in the cut zone, as shown in FIG. 6, where a scalpel 62 is being positioned to be pressed against the annuloplasty ring 10 and the ring will be backed by the shoulder surface portion shown at 15A in the cut zone. The surface portion 15A forms a reaction surface for the cutting forces or loads.

The shoulder surface portion 15A is unobstructed where flange 16 is removed, and a scalpel can be pressed toward the surface portion 15A to pass through the ring 10. A cut can be made within the scalpel cutting areas 63A, 63B which are separated by tab 21, as shown in FIG. 3. For example, a cut can be made at the dotted lines 64A and/or 64B adjacent each of the termination lines of the cut zone. The ring segment of the annuloplasty ring 10 between these lines 64, which is shown generally at 60, will be cut free of the balance or main portion of the annuloplasty ring 10 and discarded before suturing the balance or main portion into place.

When the holder is used for supporting a C-shaped annuloplasty ring, the ring 10 is supported on the holder as described above, and the ring is cut as at 64. The ring segment 60 can be removed from the holder before implanting the rest of the ring 10. If suture 34 is not cut when severing the ring 10 at 64A or 64B in cut zone 19, then suture 34 must be cut at radial grooves 30 so that ring segment 60 can be removed. The surgical sutures 98 shown in FIG. 13 can be placed through the ring and the tissue 97 on which the ring 10 is to be implanted. Then the suture 34 holding the ring 10 to the ring holder 12 is cut at grooves 32 so the ring holder can be removed. The ring 10 is then parachuted or lowered into position and the implant surgical sutures are tightened and tied off.

If the ring 10 is left as a full ring, the holder and ring are placed over the implant region and the surgical sutures 98 are put into place around the ring and the tissue 97 to which the ring is to be implanted. The release suture 34 is cut at grooves 30 and 32 and the holder removed. The ring 10 is then parachuted or lowered into position, and the surgical sutures are tightened and tied off.

Alternatively, after the holder 12 has been parachuted into position so that the annuloplasty ring 10 is surrounding a valve or similar tissue that is to be repaired, the holder 12 may be removed and the annuloplasty ring is sutured into place in a known manner by the surgeon.

When the surgeon has cut the sutures at the slots 32 and 30 in either procedure, the ring holder 12 can be removed. As the ring holder 12 is removed, the suture 34 ends that have been cut will be pulled through the annuloplasty ring 10 so that the suture lengths remain attached to the holder 12 by knots 36, 38 and 40. The knots at 36 and radial groove 30 are made so the ring segment 60 of the annuloplasty ring 10 can be removed and suture 34 will remain with the holder 12.

Figure 7:
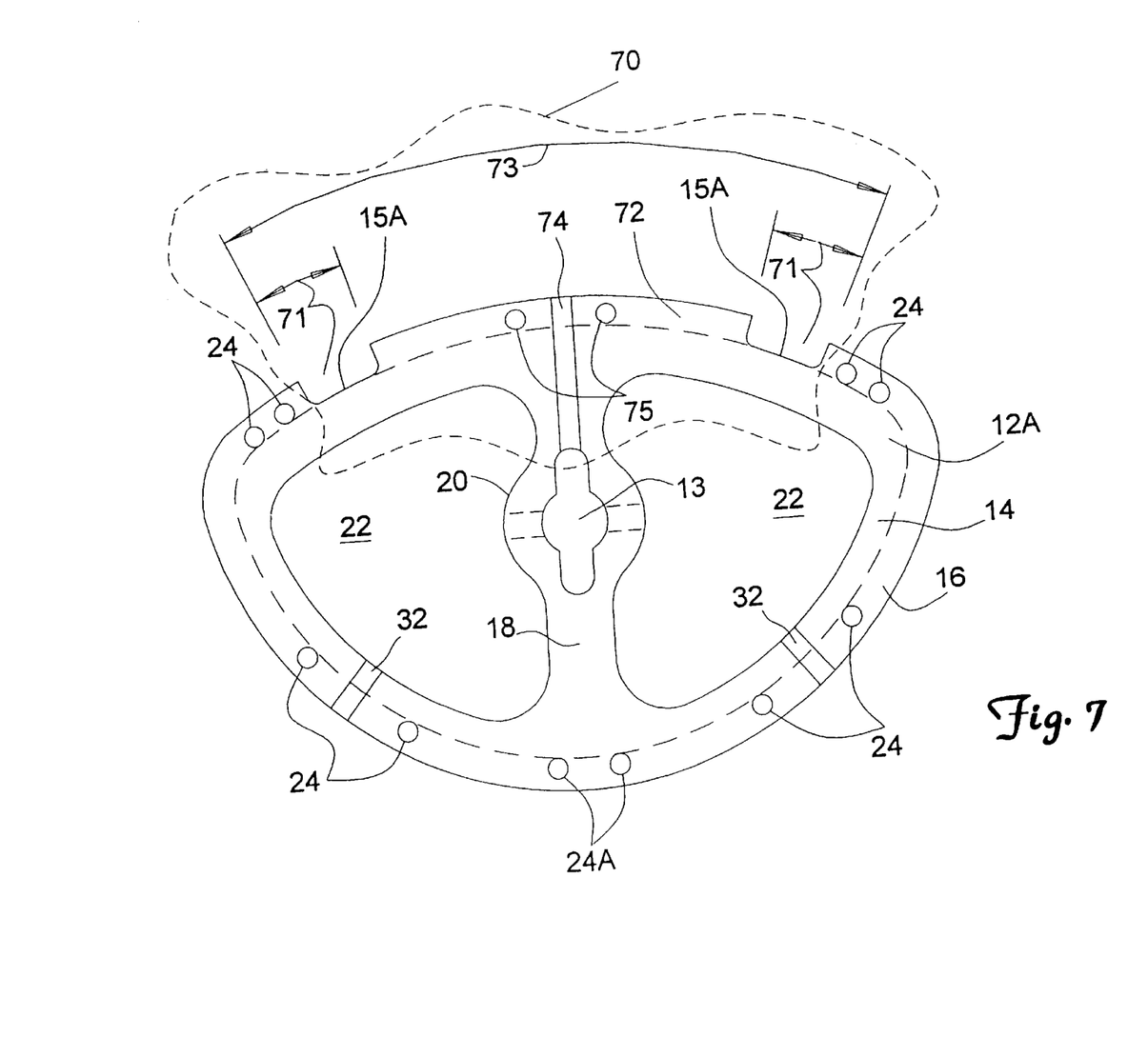
FIG. 7 is a top view of a second preferred embodiment of an annuloplasty ring holder having a modified structure in the cut zone region.
Figure 8:
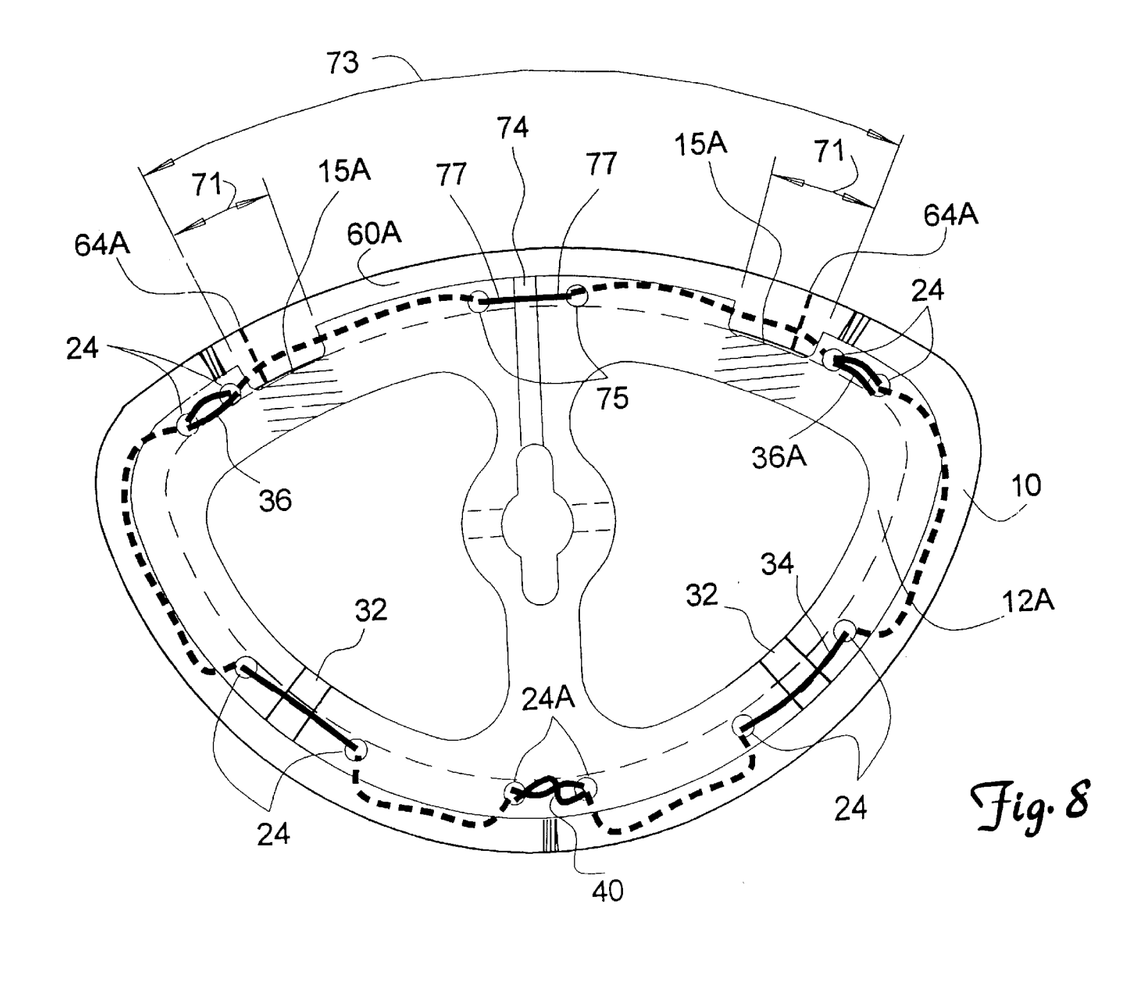
FIG. 8 is an enlarged top plan view of the device of FIG. 7 with the annuloplasty ring shown sutured in place.

FIGS. 7 and 8 show a preferred embodiment of annuloplasty ring holder 12A that has a modified cut zone region. Since the rest of the ring holder 12A is the same construction as the numbers used on holder 12, the identical parts are numbered the same. In FIGS. 7 and 8 the cut zone region is indicated at 70, by dotted lines. The annular length of the cut zone region is indicated at 73.

A tab 72 in the cut zone region 73 is widened (lengthened annularly) to provide support for ring 10 along a greater length to resist suture needle penetration forces. The two radial grooves 30 and four suture openings 27 of FIG. 1 are replaced by one groove 74 and two suture openings or bores 75, which pass through tab 72 that is the same construction as tab 21. The suture openings are the same as found at other portions of the flange 16 of the holder. Cut zone 73 is the same length as cut zone 19 in the previous embodiment, but scalpel cutting areas 71, where the flange 16 is removed, have been reduced in length.

FIG. 8 is an enlarged view showing the annuloplasty ring 10 sutured in place on the modified ring holder 12A. As before, a suture 34 is threaded through the opening 24A, then the suture is threaded as shown by dotted and solid lines proceeding clockwise, so the suture will span the first groove 32 to the left of openings 24A. First cinch knot 36 is again formed near the beginning of the scalpel cutting area 71. The suture is stitched through suture openings 75 to span groove 74 (no knot). A second cinch knot 36A is formed to the right of the cut zone 73. Before second cinch knot 36A is tightened, the suture length extending across cut zone 73 is pulled tight. The suture is carried clockwise around the holder 12A as before and back to suture opening 24A. A double surgeon's knot 40 is formed at openings 24A after pulling the suture ends tight.

If the surgeon makes use of one or both of scalpel cutting areas 71, a scalpel such as shown at 62 in FIG. 6 can be pressed directly against the ring 10 backed by surface 15A where the flange 16 is removed to pass through ring 10. For example, two cuts can be made in locations shown in FIG. 8 by the dotted lines at 64A, within scalpel cutting areas 71. The ring retention suture 34 may then be cut at groove 74, which frees cut ring segment 60A between cinch knots 36 and 36A. Cut ring segment 60 and suture sections 77 (between cuts 64 and the cut at groove 74) may then be removed as a unit from holder 12 and discarded. Alternatively, after cutting ring 10 at locations 64A, cut ring segment 60A may be removed from holder 12A and the two suture lengths 77 removed separately as one complete piece without any cutting at groove 74. Implantation of the ring with holder 12A is as described previously.

In FIGS. 9 through 12, a portion of a ring holder 12B is shown to illustrate slots formed to provide an alternate ring-to-holder attachment suturing method. Suture openings 24 in the first form of the ring, are replaced by linear or radial shaped slots 91 of FIG. 9. Horizontal cutting grooves 30, 32 are replaced with vertical grooves shown at 92. Rather than running grooves across the surface of flange 16, the cutting groove 92 extends axially (vertically) down the inside surface of the modified wall 14A, facing toward open space 22. Additional ring 10 attachment points may be created by adding horseshoe shaped grooves 94 on the bottom surface of the rim or wall 14A shown in top view in FIG. 9 and in a bottom view FIG. 10. The horseshoe groove 94 is a curved groove 94 that begins and ends at 93 on outwardly facing surface 15 (see side view FIG. 11) and which may break through the inside surface of the wall 14A so as to be open to the space 22. Horseshoe grooves 94 are optional and not required for slots 91 and cutting groove 92 to work.

Figure 12:
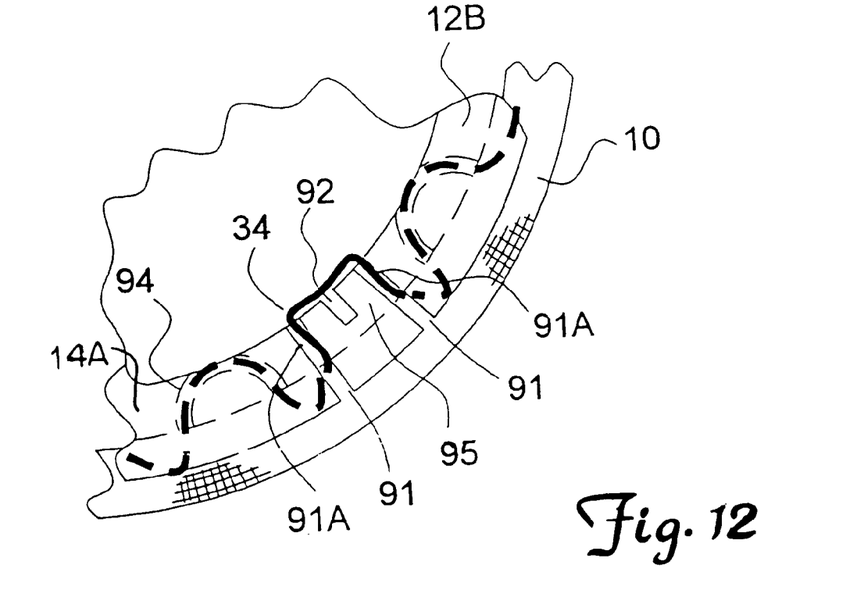
FIG. 12 is a view of the holder segment of FIG. 9 showing a suture in place with a segment of an annuloplasty ring held thereon.

FIG. 12 is a view showing a representative portion of an annuloplasty ring 10 sutured in place on the ring holder 12B. Suture 34 is stitched (as before) through the ring 10 and is threaded onto holder 12B without having to pass through any openings 24. Instead, a loop of suture is threaded through openings formed as slots 91 across cutting groove 92 on the top of holder 12B and through horseshoe grooves 94 on the bottom of the holder. Suture 34 is pulled tight and retained by previously mentioned knots such as knots 36 and 40.

This alternate attachment method allows assembly of suture 34 to ring 10 without the presence of holder 12B. Holder 12B may then be assembled to ring 10 at a later time by looping suture 34 into the grooves 94 and pulling the loop up through slots 91 to the wall 14A and passing it over the post shown at 95 that is formed by slot segments 91A, which are formed in the top part of wall 14A. The loop of suture 34 is pulled tight so it spans cutting groove 92, and then knots are tied, as before.

Figure 11:
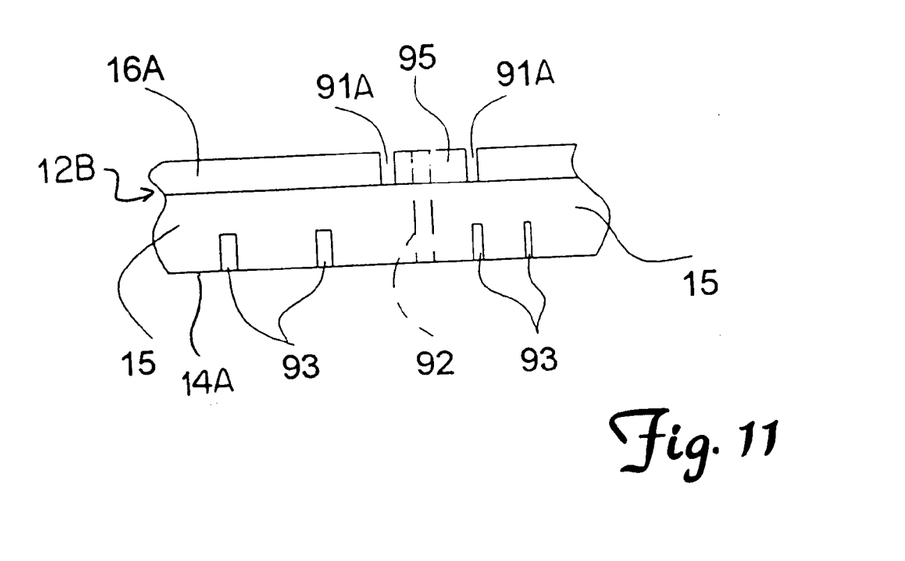
FIG. 11 is side view of the holder segment shown in FIG. 9.

The grooves 91A across wall 14A and the beginning and ends 93 of horseshoe grooves 94 are as shown in FIG. 11, and when the suture 34 is in place, as shown in FIG. 12 the suture holds the ring 10 securely to resist axial and lateral forces, in addition to the axial support provided by flange 16.

Addition of horseshoe grooves 94 to the bottom surface of rim or wall 14A increases the support of ring 10 against deforming from upward and outward radial forces during implant suture needle 99 penetration.

Figure 9:
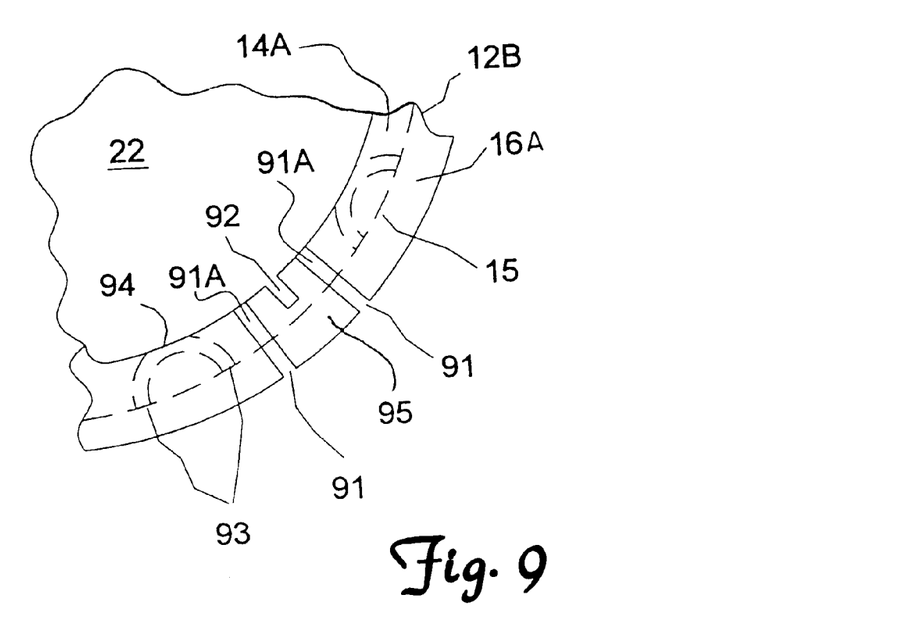
FIG. 9 is a fragmentary top view of a segment of an annuloplasty ring holder having a modified suture receiving groove.
Figure 10:
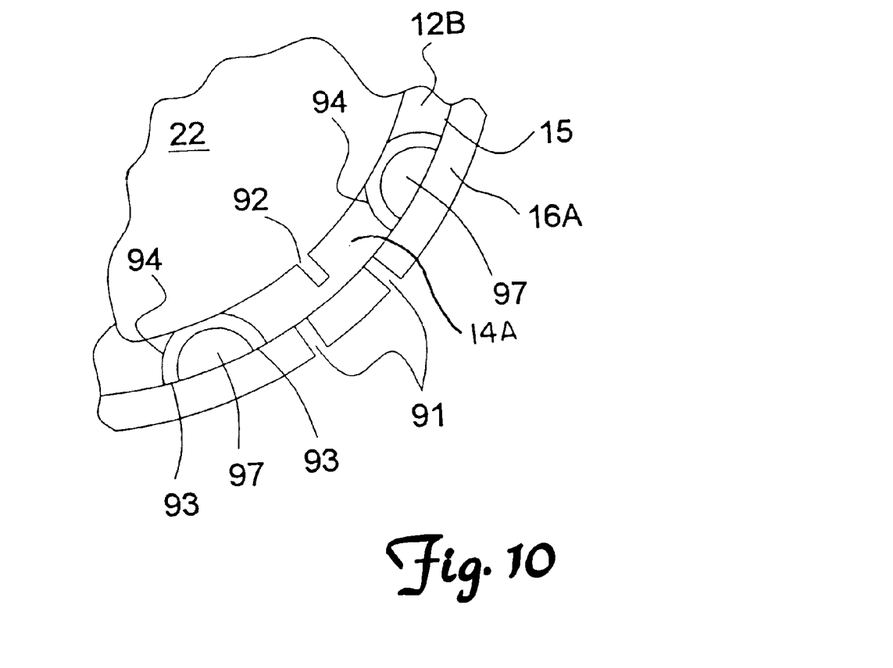
FIG. 10 is a bottom plan view of the ring segment shown in FIG. 9.

The shape of horseshoe grooves 94 forms posts 97 on the bottom side of the ring holder. The posts allow suture 34 to slide out with less resistance when suture 34 is cut for releasing ring 10. As holder 12B is withdrawn during removal from ring 10, suture 34 may also tend to drop out of horseshoe grooves 94, allowing easier removal of holder 12B. The grooves 91 and 94 can be used in the region of tab 72, if desired. The grooves 91 and 94 and the formed posts 95 and 97 are suture retainers, just as the openings 24 and 27 form suture retainers.

Figure 13:
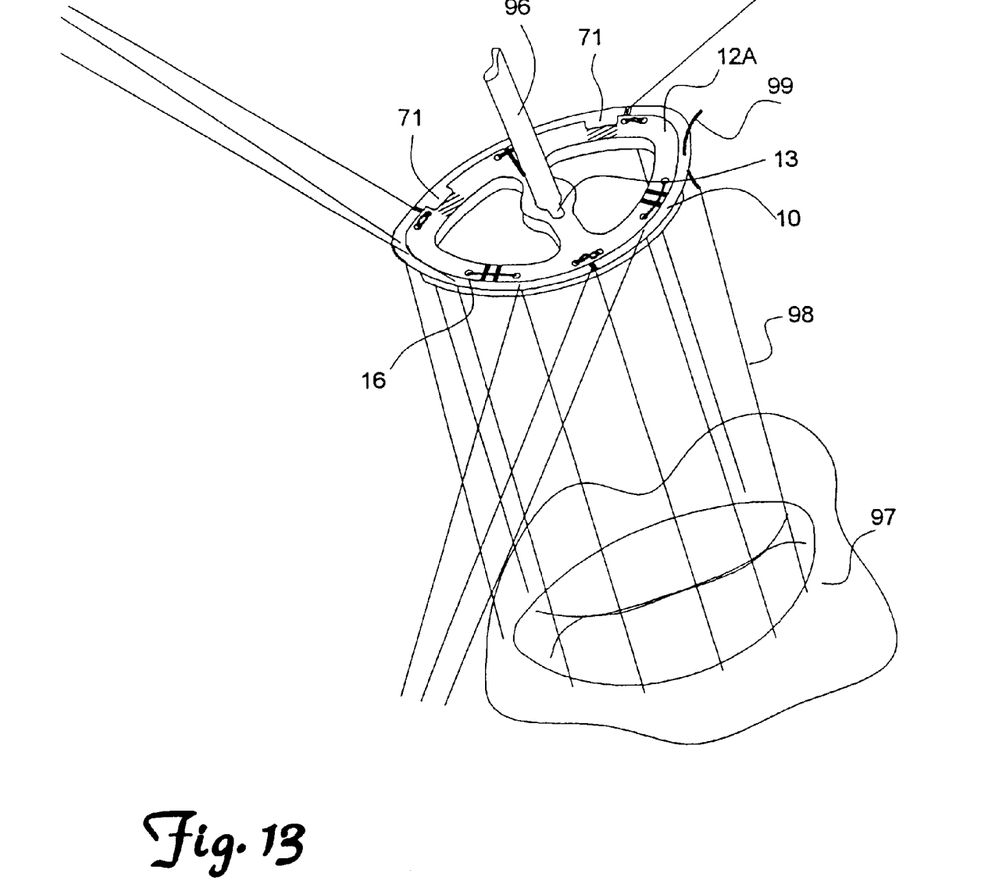
FIG. 13 is a perspective illustrative view of a step in suturing the annuloplasty ring in place on a schematically illustrated tissue annulus while retained on a ring holder made according to the present invention.

FIG. 13 illustrates the implant suturing of a ring 10 and holder 12A, as shown with the smaller scalpel cutting areas 71. The ring holder has a holder handle 96 removably attached to connector receptacle 13 and it is shown positioned above a tissue annulus 97 on which ring 10 is to be implanted. A surgical suture 98 is threaded through the tissue annulus and ring 10 with a needle 99, to form lengths of suture that, when tightened, will seat the ring 10 in place. The holder 12A can be removed by cutting the suture 34 holding the ring 10 on the holder 12A. The ring 10 then can be parachuted down the lengths of suture 98 to tissue annulus 97 and the suture 98 drawn tight and knotted.

The annuloplasty ring 10 can be any desired construction that is well known for use for suturing around heart valves, including an outer cloth covering. The annuloplasty ring can be penetrated with a needle for suturing.

Thus, the holder provides for not only supporting the annuloplasty ring in its desired shape for ease of implanting, but also provides a backing surface for cutting away portions of the annuloplasty ring 10 where desired along the shoulder surface 15A. The ring holders 12, 12A, 12B have a dual function since it can be used for implanting a full annular ring 10 or a C-shaped ring.

The annuloplasty ring may not always be sutured to the holder, and can be retained by stretching it over the holder periphery. Adhesives, staples or other attachment mechanisms also can be used for retaining the annuloplasty ring on the ring holder.

Although the present invention has been described with reference to preferred embodiments, workers skilled in the art will recognize that changes may be made in form and detail without departing from the spirit and scope of the invention.

What is claimed is:

1. An annuloplasty ring holder comprising a body having a peripheral wall including a peripheral surface for supporting an annuloplasty ring, and a flange extending from the peripheral wall along a substantial portion of the peripheral wall, and said flange terminating along at least one selected length of the peripheral wall to provide access to use the surface of the peripheral wall as a backing for forces moving against the surface.

2. The ring holder of claim 1, wherein the peripheral wall surface faces outwardly.

3. The ring holder of claim 2, wherein the flange extends outwardly from the peripheral wall along one edge of the peripheral wall surface.

4. The ring holder of claim 1, wherein the ring holder has a plurality of openings defined therein for sutures.

5. The ring holder of claim 4 including openings for sutures in the region of the length of the peripheral wall where the flange terminates.

6. The ring holder of claim 1, wherein the peripheral wall encircles an open center.

7. The ring holder of claim 6 and a reinforcing bar extending across the open center and being integral with the peripheral wall.

8. The ring holder of claim 6 and a handle connector supported within a space bounded by the peripheral wall.

9. The ring holder of claim 4, wherein the holder has a plurality of cutting grooves formed thereon and positioned between openings provided for suturing.

10. The ring holder of claim 9, wherein the cutting grooves are formed in a top surface of the holder and at least one cutting groove extending across the flange.

11. The ring holder of claim 1, wherein said surface is substantially perpendicular to a plane of the holder.

12. The ring holder of claim 7, wherein the flange is generally parallel to the plane of the holder and is flush with an upper surface of the peripheral wall.

13. An annuloplasty ring holder comprising a body having a peripheral wall including a peripheral surface for supporting an annuloplasty ring and a flange extending from the peripheral wall along a substantial portion of the peripheral wall, said flange terminating at two annularly spaced locations along the peripheral wall to provide access to use the surface of the peripheral wall as a backing for forces moving against the surface, wherein there is a tab comprising a flange section positioned between the two annularly spaced locations.

14. The ring holder of claim 13, wherein there are plurality of suture retainers on the peripheral wall, and including suture retainers aligned with said tab.

15. The ring holder of claim 1 and a plurality of suture retainers formed on the holder, including grooves on top and bottom surfaces of the peripheral wall to define posts around which sutures may be looped.

16. An annuloplasty ring assembly comprising a substantially flexible annuloplasty ring, a body defining a peripheral wall against which an annuloplasty ring is positioned and retained, said peripheral wall having a shoulder surface against which the annuloplasty ring rests, and a flange on the peripheral wall positioned at generally right angles to the shoulder surface to support the annuloplasty ring, said flange terminating at spaced locations along a selected length of the peripheral wall so that said shoulder surface is unobstructed and forms a reaction wall for cutting the annuloplasty ring at locations where the shoulder surface is unobstructed.

17. The annuloplasty ring assembly of claim 16 including a plurality of openings defined in the holder for retaining sutures to hold the annuloplasty ring against the shoulder and the flange.

18. The annuloplasty ring assembly of claim 16, wherein a side of said body has a plurality of slots extending thereacross, and wherein sutures retaining the annuloplasty ring pass across the slots.

19. An annuloplasty ring holder for supporting an annuloplasty ring, the holder including a body defining a peripheral wall against which an annuloplasty ring is positionable, suture retaining openings formed on the peripheral wall, said peripheral wall having a peripheral shoulder surface and a flange extending at generally right angles to the shoulder surface to support an annuloplasty ring, said flange terminating at spaced locations along a selected length of the peripheral wall so that said shoulder surface is unobstructed and forms a surface for supporting an annuloplasty ring on the holder under cutting forces toward the shoulder surface at locations where the shoulder surface is unobstructed.

20. The annuloplasty ring holder of claim 19 including a plurality of suture retainer openings on the body for retaining sutures to hold an annuloplasty ring against the shoulder and the flange.

21. The annuloplasty ring holder of claim 19, wherein a side of said body has a plurality of slots extending thereacross, and wherein sutures retaining an annuloplasty ring on the body pass across the slots.

22. The annuloplasty ring holder of claim 19, wherein there is a flange portion forming a tab between the spaced locations.

23. The annuloplasty ring of claim 19, wherein the peripheral wall has spaced first and second sides between which the shoulder surface extends, and a plurality of suture retainers on each of the first and second sides to retain sutures for an annuloplasty ring relative to both of said sides.

24. The annuloplasty ring holder of claim 23, wherein the suture retainer comprises posts for retaining a suture loop.

25. The annuloplasty ring of claim 24, wherein the peripheral wall has grooves formed therein to define the posts.

26. The annuloplasty ring of claim 23 wherein the suture retained by the suture retainers on first and second sides passes alternately between the first and second sides through an annuloplasty ring, to thereby resist axial and lateral forces on such annuloplasty ring.

\* \* \* \* \*